| United States Patent [19] | [11] Patent Number: 4,500,473 |
| Gauthier-Lafaye et al. | [45] Date of Patent: Feb. 19, 1985 |

[54] PREPARATION OF CARBOXYLIC ACID ANHYDRIDES

[75] Inventors: Jean Gauthier-Lafaye, Lyons; Robert Perron, Charly; Jacques Gallucci, Oullins; Philippe Leconte, Lyons, all of France

[73] Assignee: Rhone-Poulenc Chimie de Base, Courbevoie, France

[21] Appl. No.: 478,033

[22] Filed: Mar. 23, 1983

[30] Foreign Application Priority Data

Mar. 23, 1982 [FR] France ................. 82 05268

[51] Int. Cl.$^3$ ............................................. C07C 51/56
[52] U.S. Cl. ................................ 260/548; 260/398; 260/405; 260/544 A
[58] Field of Search ............... 260/544 A, 546, 548, 260/410.9 C, 398, 405

[56] References Cited

U.S. PATENT DOCUMENTS

| 2,053,233 | 9/1936 | Woodhouse | 562/519 |
| 2,727,902 | 12/1955 | Reppe et al. | 260/546 |
| 3,116,306 | 12/1963 | Heck | 260/410.9 C |
| 4,353,844 | 10/1982 | Gauthier-Lafaye et al. | 260/546 |

OTHER PUBLICATIONS

Clark, N. G., *Modern Organic Chemistry*, (1964) Oxford Univ. Press, at pp. 217 and 222.

*Primary Examiner*—Natalie Trousof
*Assistant Examiner*—L. Hendriksen
*Attorney, Agent, or Firm*—Burns, Doane, Swecker & Mathis

[57] ABSTRACT

Carboxylic acid anhydrides of the formula RCO—O—COR', e.g., acetic anhydride, are facilely prepared by reacting, in an essentially anhydrous, liquid phase containing an aprotic organic solvent, (i) a compound of the formula RX, (ii) a carboxylate of the formula $(R'COO^-)_n A^{n+}$, and (iii) carbon monoxide, said reaction being carried out in the presence of a catalytically effective amount of a salt of cobalt tetracarbonyl halide, at a temperature ranging from about 0° to 200° C. and under a pressure which is less than or equal to about 600 bars.

20 Claims, No Drawings

PREPARATION OF CARBOXYLIC ACID ANHYDRIDES

BACKGROUND OF THE INVENTION

1. Field of the Invention

The present invention relates to a novel process for the preparation of carboxylic acid anhydrides, and, more especially, to a process for the preparation of carboxylic acid anhydrides by a novel carbonylation reaction employing a cobalt-based catalyst, it being possible for the subject reaction to be carried out under relatively mild conditions of temperature and pressure.

2. Description of the Prior Art

It is well known to this art that acetic anhydride can be prepared by reacting carbon monoxide with methyl acetate in the presence of a catalyst selected from among cobalt complexes of the general formula:

$$[R_4A]_2CoX_4,$$

in which X represents a bromine or iodine atom, A represents a nitrogen or phosphorus atom and R represents a lower alkyl radical, for example (compare U.S. Pat. No. 2,730,546). However, the efficacy of this type of catalyst remains low, even though pressures in the range of from 200 to 650 bars and temperatures on the order of 180° to 190° C. are utilized.

Furthermore, French Pat. No. 1,313,360 describes various carbonylation reactions employing a salt of cobalt tetracarbonyl hydride, in a basic medium, which can all be represented by the equation:

$$RX + CO + BH \rightarrow RCOB + HX$$

in which R can be an alkyl radical, X can be a halogen atom and BH represents a molecule containing a mobile hydrogen atom (water, an alcohol, a phenol, a mercaptan, or the like). These reactions are generally carried out at atmospheric pressure or under a pressure of a few tens of bars, and at temperatures on the order of 25° to 50° C.

SUMMARY OF THE INVENTION

Accordingly, a major object of the present invention is the provision of an improved process for the preparation of carboxylic acid anhydrides by a novel carbonylation reaction catalyzed by cobalt compounds, the subject reaction being adapted to be carried out under substantially milder conditions of pressure and temperature than those hitherto required in this art.

Briefly, the present invention features a process for the preparation of carboxylic acid anhydrides having the general formula:

$$RCO-O-COR' \quad (I)$$

in which R is a linear alkyl radical having at most 4 carbon atoms and R' is a linear or branched chain alkyl radical having from 1 to 12 carbon atoms, a phenyl radical ($C_6H_5-$), a radical $C_6H_5-C_xH_{2x}-$ or a radical $C_xH_{2x+1}-C_6H_4-$, with x being an integer ranging from 1 to 6, and wherein R and R' may be identical or different, by reacting the following materials in an essentially anhydrous, liquid phase containing an aprotic organic solvent:

(i) a compound of the formula:

$$RX \quad (II),$$

in which R is as defined above and X represents an iodine atom or a group $R''-SO_3-$, R'' being an alkyl, aryl or aralkyl radical having at most 10 carbon atoms;

(ii) a carboxylate of the formula:

$$(R'COO-)_nA^{n+} \quad (III),$$

in which R' is as defined above, n is an integer equal to 1, 2, 3 or 4 and $A^{n+}$ is a cation selected from the group comprising alkali metal cations, alkaline earth metal cations, the cations $N^+R^1R^2R^3R^4$ and the cations $P^+R^1R^2R^3R^4$, in which $R^1$ to $R^4$, which are identical or different, have the same definitions as given above for R', it also being possible for $R^1$ to $R^4$ to be selected from among cycloalkyl radicals containing from 3 to 8 carbon atoms, the cation $Mn^{++}$, the cation $Zn^{++}$, the cations of metals from the lanthanide group and the cations of metals from the actinide group of the Periodic Table; and (iii) carbon monoxide; in the presence of a salt cobalt tetracarbonyl hydride [the hydride having the formula $HCo(CO)_4$], at a temperature ranging from 0° to 200° C., and under a pressure which is less than or equal to 600 bars.

DETAILED DESCRIPTION OF THE INVENTION

More particularly according to this invention, the subject process, which can be represented by the following equation:

$$RX + CO + 1/n(R'COO^-)_nA^{n+} \rightarrow RCO-O-COR' \quad (1)$$

is carried out in an essentially anhydrous, liquid phase. By the expression "essentially anhydrous, liquid phase", there is intended a medium which is liquid under the conditions of reaction and which contains the minimum possible amount of water, taking the various industrial constraints into account. It will be appreciated, however, that the presence of minor amounts of water, such as those which can be introduced in the charge or feed by technical-grade reactants, is tolerable but undesirable.

This liquid phase can be considered as being essentially homogeneous, namely, under the reaction conditions, the carbonylation process takes place in a medium in which a preponderant part of the various starting materials and of the catalyst is in solution.

As indicated above, the essentially anhydrous, liquid phase contains an aprotic organic solvent. Numerous classes of such solvents are suitable for carrying out the present invention.

More specifically, the solvents commonly referred to as "dipolar aprotic solvents", which correspond to type No. 4 in Bronsted's solvent classification scheme given in "The Chemistry of Non-Aqueous Solvents", Volume III, pages 13–16, edited by J. J. Lagowski, 1970 (Academic Press), and also carboxylic acid anhydrides, ethers or mixtures of these various compounds, are suitable for carrying out the present process.

Thus, the solvent in question can be the carboxylic acid anhydride produced or any other carboxylic acid anhydride of the above-mentioned formula (I). Acetic anhydride is more particularly suitable as a solvent for carrying out the subject process.

The solvent in question can also be selected from among cyclic ethers such as dioxane, tetrahydrofuran and macrocyclic ethers more commonly referred to as crown ethers, or alternatively from among the polyethylene glycol alkyl ethers of the formula:

$$R^5-O-(CH_2-CH_2-O)_y-R^6 \quad (IV)$$

in which $R^5$ and $R^6$, which are identical or different, have the same definitions as given above for R, with y being an integer ranging from 1 to 8. Exemplary of the polyethylene glycol alkyl ethers which are representative for carrying out the subject process are: ethylene glycol dimethyl ether (commonly referred to as glyme), diethylene glycol dimethyl ether, diethylene glycol diethyl ether, diethylene glycol dibutyl ether, diethylene glycol ethyl butyl ether, triethylene glycol dimethyl ether and tetraethylene glycol dimethyl ether (tetraglyme).

The solvent can also be appropriately selected from among the sulfones of the formula:

(V)

in which $R^7$ and $R^8$, which are identical or different, have the same definitions as given above for $R'$; $R^7$ and $R^8$ can also together form a single divalent alkylene or alkenylene radical containing from 3 to 6 carbon atoms (for example, a tetramethylene or hexamethylene radical) and, if appropriate, 1 or 2 ethylenic double bonds, it being possible for the said radical to contain 1 to 3 alkyl substituents having from 1 to 4 carbon atoms. Dialkyl sulfones, namely, compounds of the above formula (V) in which $R^7$ and $R^8$, which are identical, are linear alkyl radicals, are particularly suitable for carrying out the process according to the invention, and tetramethylenesulfone, 3-methyltetramethylenesulfone, 2,4-dimethyltetramethylenesulfone and mixtures thereof are more particularly suitable.

Furthermore, the solvent can be selected equally as well from among the carboxylic acid amides of the formula:

(VI)

in which $R^9$, $R^{10}$ and $R^{11}$, which are identical or different, have the same definitions as given above for $R'$; two of the radicals $R^9$, $R^{10}$ or $R^{11}$ can also together form a single divalent radical $(-CH_2)_z-$, z being an integer ranging from 3 to 12; $R^9$ can also represent a hydrogen atom or a radical of the formula:

(VII)

in which $R^{12}$ and $R^{13}$, which are identical or different, represent alkyl radicals having at most 4 carbon atoms. Examples of such solvents which are representative are: tetramethylurea, N,N-dimethylformamide, N,N-dimethylacetamide, N,N-diethylacetamide, N,N-dicyclohexylacetamide, N,N-dimethylpropionamide, N,N-diethylpropionamide, N,N-diethyl-n-butyramide, N,N-dimethylbenzamide, N,N-dicyclohexylbenzamide, N,N-diethyl-m-toluamide, N-acetylpyrrolidine, N-acetylpiperidine, N-(n-butyryl)-piperidine, N-methylpyrrolidin-2-one, N-ethylpyrrolidin-2-one, N-methylpiperidin-2-one and N-methylepsilon-caprolactam.

The solvent can also be selected from among the nitriles of the formula:

$$R^{14}-CN \quad (VIII)$$

in which $R^{14}$ has the same definition as given above for $R'$. Exemplary of such compounds, representative are acetonitrile and benzonitrile.

The selection from among the aforesaid numerous categories of solvents will be governed above all by considerations of a practical nature, such as the solubility of the starting materials used, in the solvent in question, and the ease of separation of the product from the solvent in question.

The reaction is advantageously carried out in the presence of a solvent selected from among acetic anhydride, tetramethylenesulfone and N-methylpyrrolidin-2-one.

Thus, according to the present invention, one starting material is a compound of the formula RX, in which R is a linear alkyl radical having at most 4 carbon atoms and X represents an iodine atom or a group $R''-SO_3-$, $R''$ being an alkyl, aryl or aralkyl radical having at most 10 carbon atoms. Exemplary of such reactants, representative are methyl iodide, N-butyl iodide, methyl methanesulfonate, methyl ethanesulfonate, ethyl ethanesulfonate, methyl benzenesulfonate, methyl p-toluenesulfonate, n-butyl benzenesulfonate, n-butyl p-toluenesulfonate and methyl phenylmethanesulfonate.

Alkyl iodides and alkyl p-toluenesulfonates are more particularly suitable for carrying out the present process. Methyl iodide is a more particularly suitable reactant within the scope of this invention.

Another starting material used for carrying out the subject process is a carboxylate of the formula:

$$(R'CO-O^-)_n A^{n+} \quad (III)$$

in which $R'$, $A^{n+}$ and n are as above-defined.

A first category of carboxylates which can be used in accordance with the process of the invention consists of alkali metal carboxylates and alkaline earth metal carboxylates. Exemplary of such compounds are the acetates of lithium, sodium, potassium, calcium and magnesium, sodium benzoate and sodium phenylacetate.

A second category of carboxylates which can be used in the process of the invention consists of the carboxylates of metals from the lanthanide and actinide groups of the Periodic Table. Examples of such compounds are the acetates of lanthanum, cerium and thorium.

A third category of carboxylates useful in the subject process consists of quaternary ammonium carboxylates and quaternary phosphonium carboxylates, in which the cations are represented respectively by the formulae $N^+R^1R^2R^3R^4$ and $P^+R^1R^2R^3R^4$, $R^1$ to $R^4$ being as above-defined at the beginning of the present specification. The precise nature of the quaternary phosphonium (or ammonium) cation is not of fundamental importance. The selection from among the various quaternary phosphonium (or ammonium) cations will be governed above all by considerations of a practical nature, such as the accessibility or ease of preparation of the corresponding carboxylates and how convenient the compounds in question are to use. If it is desired to use a carboxylate of this type, derivatives of the methyltriphenylphosphonium cation or of the methyltriethylammonium cation will be selected, for the various reasons mentioned above, although, in principle, any other cation of this type is also suitable for carrying out this invention.

On the other hand, the selection of the precise nature of the carboxylate anion will be governed above all by the nature of the desired products. In fact, as shown by equation (1) at the beginning of the present specification, it is possible, by carrying out the present process, to obtain carboxylic acid anhydrides which can be either symmetrical (if R and R' are identical) or asymmetrical (if R and R' are not identical). Now, it is well known to those skilled in the art that the asymmetrical anhydride can be converted by heating to give the two corresponding symmetrical anhydrides according to the equation:

$$2RCO-O-COR' \rightarrow (RCO)_2O + (R'CO)_2O \qquad (2)$$

in which R and R' are as above-defined.

Within the scope of the particular application of the present process to the preparation of acetic anhydride, it is apparent that it will be preferred to use alkali metal or alkaline earth metal acetates or the acetates of lanthanum, cerium or thorium, with the alkali metal acetates proving to be the more particularly preferred.

In general, beyond this particular application, it is preferred to use the alkali metal carboxylates.

The concentration of the carboxylate of the formula (III) in the aprotic solvent typically ranges from 0.1 to 5 mols per liter, and preferably ranges from 0.25 to 3 mols per liter for improved results.

In the present process, therefore, a compound of the formula (II), a carboxylate of the formula (III) and carbon monoxide are brought into contact in an essentially anhydrous, liquid phase containing an aprotic solvent. It is preferred to use carbon monoxide in the essentially pure form, as available commercially. However, the presence of impurities, such as carbon dioxide, oxygen, methane and nitrogen, can be tolerated. The presence of hydrogen is not harmful, even in relatively large proportions, but these proportions must not exceed 15 mol% in the mixture of gases.

As shown by equation (1), it is theoretically necessary to use 1/n mol of carboxylate of the formula (III) and 1 mol of carbon monoxide per mol of compound of the formula (II) in order to produce 1 mol of anhydride. Of course, the proportions of the various reactants can deviate widely from these values, and it is possible, for example, to use an excess of carbon monoxide. Likewise, it is possible to use an excess of compound of the formula (II) or of carboxylate of the formula (III). In general, the molar ratio of the compound of the formula (II) to the carboxylate anion (R'COO−) ranges from 0.5 to 2 and, to carry out the invention with good results, it will be close to the stoichiometric ratio (1).

The subject reaction takes place in the presence of a salt of cobalt tetracarbonyl hydride [HCo(CO)₄].

The salts of cobalt tetracarbonyl halide can be represented by the formula:

$$M^{p+}[Co(CO)_4]_p \qquad (IX)$$

in which p is an integer equal to 1 or 2 and $M^{p+}$ is a cation selected from the group comprising alkali metal cations, alkaline earth metal cations, the cations $N^+R^1R^2R^3R^4$, the cations $P^+R^1R^2R^3R^4$, $R^1$ to $R^4$ being as defined above, the cations $Ag^+$, $Mn^{2+}$, $Zn^{2+}$ and $Co^{2+}$ and the cation $Hg^{2+}$.

Without wishing to be bound to any particular theoretical mechanism, it is reasoned that the anion $[Co(CO)_4]^-$ plays an important role in the course of the reaction, and that the precise nature of the caption $M^{p+}$ is not of fundamental importance within the scope of the subject process. The selection from among the various possible cations is governed above all by considerations of a practical nature, relating to the preparation of the corresponding salts.

These salts can be prepared separately or formed in situ. The salts of cobalt tetracarbonyl hydride, which are preferably prepared at the time of use, are for the most part known compounds. Various methods for the preparation of these compounds are described in the literature. Thus, reference is made to the article by J. A. Gladysz et al. published in *Inorganic Chemistry*, Volume 18, No. 3, pages 553–558 (1979), for the preparation of alkali metal salts of cobalt tetracarbonyl hydride (tetracarbonylcobaltates of lithium, potassium or sodium), and to the article by D. H. Gibson et al published in *Journal of Organometallic Chemistry*, 206, pages C17–C20 (1981), for the preparation of quaternary ammonium salts of cobalt tetracarbonyl hydride. The latter method can also be used for the preparation of quaternary phosphonium salts of cobalt tetracarbonyl hydride. (The modification which has to be made to the method described will be immediately apparent to those skilled in the art).

Of course, as is known, the salts of cobalt tetracarbonyl hydride can be formed in situ, under the reaction conditions, from cobalt compounds which are more common and, in certain cases, commercially available. In fact, salts of cobalt (+2), such as cobalt halides, cobalt acetylacetonate, cobalt acetate, basic cobalt carbonate and cobalt naphthenate, can be reduced to $[Co(CO)_4]^-$, for example, with manganese powder and sodium thiosulfate ($Na_2S_2O_3$). Dicobalt octacarbonyl, $Co_2(CO)_8$, can also constitute an effective source of tetracarbonylcobaltate under the reaction conditions.

The salts of cobalt tetracarbonyl hydride can be used in the solid state or alternatively in the form of their solution in the solvent selected for carrying out the carbonylation reaction.

As indicated above, the precise nature of the cation $M^{p+}$ of the salt of cobalt tetracarbonyl hydride is not critical. Examples of salts which can be used within the scope of the present process are: sodium tetracarbonylcobaltate, lithium tetracarbonylcobaltate, potassium tetracarbonylcobaltate and methyltriphenylphosphonium tetracarbonylcobaltate.

The amount of catalyst to be used is not of fundamental importance. For example, it is possible to use 1 gram atom of cobalt or more per mol of compound of the formula (II). However, to carry out the invention with good results, the amount of catalyst, expressed in milligram atoms of cobalt per mol of compound of the formula (II), will range from 2 to 1,000 and preferably from 5 to 100.

The reaction temperature will generally range from 0° to 200° C. and preferably from 20° to 150° C. To carry out the process according to the invention with good results, a temperature close to ambient temperature (about 25° C.) will be selected if it is desired to use, as the starting material, a carboxylate of the formula (III) in which the cation is selected from among the cations of the formulae $N^+R^1R^2R^3R^4$ and $P^+R^1R^2R^3R^4$, in which $R^1$ to $R^4$ are as defined above. On the other hand, if an alkali metal carboxylate is used, it will prove advantageous to carry out the reaction at a temperature above 50° C.

The pressure at the selected temperature can vary over wide limits, for example, from 0.01 to 600 bars. It will preferably range from 0.5 to 100 bars and more preferably from 1 to 50 bars.

To carry out the process according to the invention, it is possible, for example, to introduce the compound of the formula (III), the salt of cobalt tetracarbonyl hydride, the reaction solvent and the carbon monoxide into a suitable reactor, to heat the mixture to the selected temperature, and then, in a second stage, to introduce the carboxylate. This procedure is mode particularly suitable in the case where the cation of the carboxylate is a cation of the formula $P^+R^1R^2R^3R^4$ or $N^+R^1R^2R^3R^4$, with $R^1$ to $R^4$ being as above-defined.

It is also possible to introduce the reactants, the reaction solvent, the catalyst and carbon monoxide into the appropriate apparatus, and then to heat the entire mass to the selected temperature.

Upon completion of the reaction, the anhydride produced can be separated off by any suitable means, for example, by distillation.

The process according to the invention has a particular application in the preparation of acetic anhydride by the reaction of methyl iodide, an alkali metal acetate and carbon monoxide. By carrying out the present process, it is in fact possible to obtain acetic anhydride by means of a carbonylation reaction at a temperature below 100° C. and under a total pressure, at the reaction temperature, of less than 50 bars, by using a cobalt-based catalyst.

In order to further illustrate the present invention and the advantages thereof, the following specific examples are given, it being understood that same are intended only as illustrative and in nowise limitative.

EXAMPLES (i) Preparation of methyltriphenylphosphonium acetate:

10 millimols of methyltriphenylphosphonium iodide, 10 millimols of silver acetate and 25 ml of acetonitrile were introduced into a round-bottomed flask of 50 ml capacity, under argon.

The flask was heated to 50° C. by means of a waterbath; the mixture was maintained at this temperature for 3 hours. It was subsequently cooled and then filtered in order to remove the silver iodide which had precipitated. The filtrate was recovered. Infra-red analysis of the solution evidenced the existence of bands corresponding to the presence of methyltriphenylphosphonium acetate.

The solvent was evaporated off in vacuo. A brown paste was obtained. This paste could be used as such, or after it had been redissolved in the selected solvent.

(ii) Preparation of lithium tetracarbonylcobaltate:

40 ml of dry tetrahydrofuran, 0.72 millimol of dicobalt octacarbonyl and then 1.6 ml of a solution of 1 mol of lithium triethylborohydride in tetrahydrofuran were introduced, under argon, into a 100 ml round-bottomed flask. The mixture was stirred at about 25° C. for 30 minutes.

After the evolution of hydrogen had ceased, the stirring was terminated, the solution was filtered under argon and the solvent was driven off. The residue was then dried under a vacuum of 0.5 mm Hg at 100° C. for 30 minutes.

A portion of the solid was taken up in 10 ml of acetonitrile. Infra-red analysis of the solution evidenced the bands characteristic of the tetracarbonylcobaltate anion.

(iii) Preparation of methyltriphenylphosphonium tetracarbonylcobaltate:

5 millimols of dicobalt octacarbonyl were dissolved in 250 ml of methylene chloride. The filtrate was run into a solution of 250 ml of distilled water containing 60 millimols of sodium borohydride and 15 millimoles of methyltriphenylphosphonium chloride. The solution was stirred at ambient temperature for about 3 hours. After settling, the organic phase was separated off, washed 4 times with 100 ml of deoxygenated water and then dried overnight over $Na_2SO_4$.

The solvent was evaporated off and the residual solid was dissolved in 30 ml of n-butanol at about 100° C. and recrystallized.

The crystals were filtered off and washed with 30 ml of hexane. After drying, 3.1 g of methyltriphenylphosphonium tetracarbonylcobaltate were isolated, this being a yield of 69%.

Hereafter, r will denote the molar ratio $RX/R'COO^-$ and RY (%) will denote the number of mols of anhydride formed per 100 mols of the reactant which was not introduced in excess.

EXAMPLE 1

A solution of 0.6 millimol of lithium tetracarbonylcobaltate $[Li^+Co^-(CO)_4]$ in 1 ml of acetonitrile was introduced into a glass round-bottomed flask of 50 ml capacity. 8 millimols of methyl iodide were added, carbon monoxide being bubbled into the solution at the same time. After stirring for 15 minutes at ambient temperature, a solution of 0.8 millimol of methyltriphenylphosphonium acetate in 2 ml of acetonitrile was introduced into the flask, the stream of carbon monoxide being maintained for 15 minutes (r=10).

After a reaction time of 12 hours at ambient temperature, the resulting reaction mixture was analyzed by gas chromatography. It contained 0.3 millimol of acetic anhydride, which corresponded to a yield of 38% relative to the methyltriphenylphosphonium acetate introduced.

EXAMPLE 2

Example 1 was repeated, using a solution of 1 millimol of methyltriphenylphosphonium tetracarbonylcobaltate, of the formula $CH_3P^+(C_6H_5)_3Co^-(CO)^4$, in 10 ml of glyme (ethylene glycol dimethyl ether), 10 millimols of methyl iodide and 12 millimols of sodium acetate, carbon monoxide being bubbled therethrough (r=0.83).

After a reaction time of 15 hours at ambient temperature, gas chromatographic analysis of the resulting reaction mixture evidenced that it contained 1.5 millimols of acetic anhydride, which corresponded to a yield of 15% relative to the methyl iodide introduced.

EXAMPLE 3

An experiment was carried out using the procedure described in Example 1 and starting with 29 millimols of methyl iodide, a solution of 1 millimol of methyltriphenylphosphonium tetracarbonylcobaltate in 40 ml of N-methylpyrrolidin-2-one, and 23 millimols of sodium acetate, carbon monoxide being bubbled therethrough (r=1.26). After a reaction time of 4 hours at 60° C., the total pressure at the reaction temperature being on the order of 1 bar, gas chromatographic analysis of the resulting reaction mixture evidenced that it contained 1.4 millimols of acetic anhydride, which corresponded to a yield of 6% relative to the sodium acetate introduced.

EXAMPLE 4

Example 3 was repeated, using 32 millimols of methyl iodide, a solution of 1 millimol of methyltriphenylphosphonium tetracarbonylcobaltate in 40 ml of glyme, and 32 millimols of sodium acetate, carbon monoxide being bubbled therethrough (r=1).

This provided 1.5 millimols of acetic anhydride, the same being a yield on the order of 5% relative to either one of the reactants introduced.

EXAMPLES 5 TO 9

Control experiment (a)

A series of experiments was carried out according to the following procedure:

Methyl iodide, 30.5 millimols of sodium acetate, 1 millimol of methyltriphenylphosphonium tetracarbonylcobaltate and 30 ml of a solvent were introduced into a titanium autoclave of 75 ml capacity. After the autoclave had been closed, a carbon monoxide pressure of 22 bars was applied. Stirring by means of a reciprocating system was commenced and the autoclave was heated to 60° over about 20 minutes by means of an annular furnace. The total pressure at the reaction temperature was then equal to 25 bars. It was maintained constant and equal to 25 bars by successively introducing additional amounts of carbon monoxide. After a reaction time of 2 hours at the temperature indicated, the stirring was terminated; the autoclave was cooled and degassed.

The reaction mixture was then analyzed either by gas chromatography or by potentiometry. In Example 9, the results indicated were determined from the number of mols of carbon monoxide absorbed during the reaction time of 2 hours at the reaction temperature.

The particular conditions and also the results obtained are reported in Table I below.

The column headed "Determination" indicates the method of "analysis" as follows:
1: absorption of the carbon monoxide
2: gas chromatography
3: potentiometry.

Control experiment (a), carried out in acetic acid, does not fall within the scope of the present invention; no absorption of the carbon monoxide was observed in this experiment.

TABLE I

| Example No. | CH$_3$I mmol | r | Solvent (*) | Determination | Ac$_2$O mmol | RY (%) |
|---|---|---|---|---|---|---|
| 5 | 32 | 1.08 | glyme | 2 | 23.7 | 78 |
| 6 | 33.9 | 1.11 | NMP | 2 | 13.8 | 45 |
| 7 | 32 | 1.05 | TMS | 3 | 23.0 | 75.4 |
| 8 | 32 | " | acetonitrile | 2 | 22.5 | 73.7 |
| 9 | 33 | 1.08 | Ac$_2$O | 1 | 25.0 | 82.0 |

TABLE I-continued

| Example No. | CH$_3$I mmol | r | Solvent (*) | Determination | Ac$_2$O mmol | RY (%) |
|---|---|---|---|---|---|---|
| a | 32.9 | " | AcOH | 1 | 0 | 0 |

(*): NMP = N—methylpyrrolidin-2-one
TMS = tetramethylenesulfone
Ac$_2$O = acetic anhydride
AcOH = acetic acid

EXAMPLE 10

Example 6 was repeated, with the following modifications to the charge: CH$_3$I=27 millimols; AcONa=30 millimols (r=0.9); methyltriphenylphosphonium tetracarbonylcobaltate=3 millimols.

After the autoclave had been closed, a carbon monoxide pressure of 45 bars was applied; the pressure at a temperature of 60° C. was maintained at 50 bars.

This provided 9.4 millimols of acetic anhydride [RY (%)=35], all other conditions being equal.

EXAMPLES 11 TO 15

In a Hastelloy B2 autoclave of 125 ml capacity, a series of experiments was carried out on a charge consisting of methyl iodide, sodium acetate, 50 ml of glyme and 1 millimol of methyltriphenylphosphonium tetracarbonylcobaltate, the procedure employed being analogous to that described for Examples 5 to 9. The particular conditions and also the results obtained in a reaction time of 2 hours at 60° C. under a total pressure, at the reaction temperature, which was maintained at 25 bars by successively introducing additional amounts of carbon monoxide, are reported in Table II below. Analysis of the resulting reaction mixtures was carried out by gas chromatography.

TABLE II

| Example No. | AcONa mmol | CH$_3$I mmol | r | Acetic anhydride mmol | RY (%) |
|---|---|---|---|---|---|
| 11 | 50 | 48.9 | 0.98 | 48 | 98.0 |
| 12 | " | 24.1 | 0.48 | 22.7 | 94.2 |
| 13 | " | 10.8 | 0.22 | 8.4 | 77.7 |
| 14 | 12.2 | 49.2 | 4.03 | 12.2 | 100.0 |
| 15 | 100 | 48.9 | 0.49 | 44.1 | 90.2 |

EXAMPLES 16 TO 20

Control experiment (b)

Using the autoclave and procedure described for Examples 11 to 15, a series of experiments was carried out under the following common conditions:

The charge consisted of 50 ml of tetramethylenesulfone, 1 millimol of methyltriphenylphosphonium tetracarbonylcobaltate, methyl iodide and a metal acetate, the nature and amount of which are reported in Table III below.

After the autoclave had been closed, a carbon monoxide pressure of 22 bars was applied. The reaction temperature was 60° C. The total pressure at the reaction temperature was 25 bars and same was maintained at this value by successively introducing additional amounts of carbon monoxide. The reaction time at the reaction temperature was 2 hours.

The particular conditions and also the results obtained are reported in Table III below, in which the column headed "Determination" has the meaning indicated above.

No absorption was observed over the course of control experiment (b).

TABLE III

| Example No. | METAL ACETATE nature | mmol | CH$_3$I mmol | r | Determination | ACETIC ANHYDRIDE mmol | RY (%) |
|---|---|---|---|---|---|---|---|
| 16 | Zn(OAc)$_2$ | 50 | 49 | 0.49 | 2 | 1.3 | 2.7 |
| 17(x) | Mn(OAc)$_2$ | 50 | 48.3 | 0.48 | 2 | 8.0 | 16.6 |
| 18 | Mg(OAc)$_2$ | 50 | 50 | 0.50 | 2 | 7.0 | 14.0 |
| 19(x) | NaOAc | 50 | 49.1 | 0.98 | 3 | 40.3 | 82.0 |
| 20 | LiOAc | 33 | 48 | 1.45 | 3 | 24.8 | 75.0 |
| b | Cr(OAc)$_3$ | 50 | 49 | 0.33 | 1 | 0 | 0 |

(x) the metal acetate had been preliminarily dried in vacuo at 100° C.

EXAMPLES 21 TO 24

In a tantalum autoclave of 125 ml capacity, a series of experiments was carried out starting from different sodium carboxylates (R'COONa) in an amount of about 1 mol/liter, and from various compounds of the formula RX, using 1 millimol of methyltriphenylphosphonium tetracarbonylcobaltate and using a procedure analogous to that described for Examples 16 to 20. The pressure at the reaction temperature was maintained at 50 bars. Upon completion of Experiments 21 to 23, the number of millimols of anhydride groups (—CO—O—CO—) was determined; for Experiment No. 24, the number of millimols of acetic anhydride present in the reaction mixture was determined.

The particular conditions and also the results obtained are reported in Table IV below, in which:
Ph denotes a phenyl radical
OTs denotes a tosylate radical
TMS denotes tetramethylenesulfone.

The "pressure applied" was the carbon monoxide pressure applied before bringing the autoclave to the reaction temperature.

The numbers indicated in the row headed "Determination have the meaning given for Examples 5 to 9.

TABLE IV

| Example No. | 21 | 22 | 23 | 24 |
|---|---|---|---|---|
| RX: (mmol) | CH$_3$I (45.9) | CH$_3$I (45.8) | n-C$_4$H$_9$I (46.2) | CH$_3$OTs (50) |
| R'COONa: (mmol) | Ph—CH$_2$—COONa (50) | Ph—COONa (50) | CH$_3$—COONa (50) | CH$_3$COONa (50) |
| r | 0.92 | 0.92 | 0.92 | 1 |
| Solvent: (ml) | glyme (50) | glyme (45) | TMS (50) | glyme (50) |
| Pressure applied | 42 bars | 42 bars | 37 bars | 42 bars |
| Temperature | 80° C. | 80° C. | 120° C. | 83° C. |
| Time at the reaction temperature | 1 hour | 2 hours | 2 hours | 1 hour, 40 minutes |
| Determination | 3 | 3 | 3 | 2 |
| Anhydride in mmol | 23.8 | 40.1 | 28 | 6.4 |
| Anhydride RY (%) | 51.8 | 87.6 | 60.6 | 12.8 |

EXAMPLE 25

This example illustrates the use of a catalyst formed in situ from dicobalt octacarbonyl.

50 ml of tetramethylenesulfone, 51.1 millimols of methyl iodide, 50 millimols of sodium acetate dried beforehand (r = 1.02), 2 millimols of dicobalt octacarbonyl and 3 millimols of sodium iodide were introduced into a tantalum autoclave of 125 ml capacity. A carbon monoxide pressure of 23 bars was applied. Stirring was commenced and the autoclave was heated to 65° C. over about 20 minutes. The total pressure at the reaction temperature was maintained constant and equal to 25 bars by successively introducing additional amounts of carbon monoxide. After a reaction time of 1 hour at the reaction temperature, the stirring was terminated; the autoclave was cooled and degassed.

Gas chromatographic analysis of the resulting reaction mixture evidenced that it contained 39.4 millimols of acetic anhydride, this being a yield of 79% relative to the methyl iodide introduced.

EXAMPLES 26 TO 28

Control experiment (c):

In a 125 ml autoclave made of Hastelloy B2 (denoted by HB2 in Table V below) or made of tantalum (denoted by Ta in this table), a series of experiments was carried out at 70° C., under a pressure, at the reaction temperature, which was maintained constant and equal to 41 bars by successively introducing additional amounts of carbon monoxide, on a charge consisting of methyl iodide, a metal acetate, the nature and amount of which are specified in Table V below, 50 ml of N-methylpyrrolidone and dicobalt octacarbonyl.

The particular conditions and also the results obtained by means of gas chromatographic analysis are also reported in Table V below.

TABLE V

| Example No. | Autoclave | METAL ACETATE nature | mmol | CH$_3$I mmol | r | Time minutes | ACETIC ANHYDRIDE mmol | RY (%) |
|---|---|---|---|---|---|---|---|---|
| 26 | HB2 | La(OAc)$_3$ | 17 | 49.8 | 0.97 | 120 | 36 | 72 |
| 27 | Ta | Th(OAc)$_4$ | 18.9 | 46.5 | 0.61 | 140 | 42.8 | 92 |
| 28 | Ta | Zn(OAc)$_2$ | 40 | 44.1 | 0.55 | 30 | 30.9 | 70 |
| c | HB2 | Cr(OAc)$_3$ | 17 | 49.3 | 0.97 | 70 | 0 | 0 |

EXAMPLES 29 AND 30

Examples 22 and 23 were repeated, but the methyltriphenylphosphonium tetracarbonylcobaltate was replaced by the dicobaltoctacarbonyl and the pressure was maintained, at the reaction temperature, at 50 bars (Example 29) and 80 bars (Example 30). Upon completion of each experiment, the anhydride functions present were identified by potentiometry, and the various anhydrides formed were determined by proton Nuclear Magnetic Resonance (NMR).

The particular conditions and the results obtained are reported in the Table IV which follows, in which:

Ph denotes a phenyl radical

The pressure applied was the pressure of the carbon monoxide before the autoclave was heated to reaction temperature.

TABLE VI

| EXAMPLE | 29 | 30 |
| --- | --- | --- |
| RX (mMol) | CH$_3$I (49) | n-C$_4$H$_9$I (48) |
| R'COONa (mMol) | PhCOONa (50) | CH$_3$COONa (50) |
| r | 0.96 | 0.96 |
| Solvent ml | glyme (45) | glyme (45) |
| Pressure applied | 42 bars | 59 bars |
| Temperature | 80° C. | 120° C. |
| Time at the reaction temperature | 35 minutes | 45 minutes |
| Determination by proton NMR | PhCOOCOCH$_3$ = 50% CH$_3$COOCOCH$_3$ = 25% PhCOOCOPh = 25% | nC$_4$H$_9$COOCOCH$_3$ = 50% CH$_3$COOCOCH$_3$ = 25% (nC$_4$H$_9$CO)$_2$O = 25% |
| Anhydride in mMol | 24 | 38 |
| Anhydride RY (%) | 49 | 79 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a carboxylic acid anhydride having the general formula:

$$RCO-O-COR' \qquad (I)$$

in which R is a linear alkyl radical having at most 4 carbon atoms and R' independently is a linear or branched chain alkyl radical having from 1 to 12 carbon atoms, a phenyl radical (C$_6$H$_5$—), a radical C$_6$H$_5$—C$_x$H$_{2x}$— or a radical C$_x$H$_{2x+1}$—C$_6$H$_4$—, with x being an integer ranging from 1 to 6, which process comprises:

reacting, in an essentially anhydrous, liquid phase containing an aprotic organic solvent:

(i) a compound of the formula:

$$RX \qquad (II)$$

in which R is as above-defined and X is an iodine atom or a group R''—SO$_3$—, with R'' being an alkyl, aryl or aralkyl radical having at most 10 carbon atoms;

(ii) a carboxylate of the formula:

$$(R'COO^-)_nA^{n+} \qquad (III)$$

in which R' is as above-defined, n is an integer ranging from 1 to 4, and A$^{n+}$ is an alkali metal cation, an alkaline earth metal cation, a cation N$^+$R$^1$R$^2$R$^3$R$^4$ or a cation P$^+$R$^1$R$^2$R$^3$R$^4$, in which R$^1$ to R$^4$, which may either be identical or different, each have the definition given above for R', or may be a cycloalkyl radical having from 3 to 8 carbon atoms, the cation Mn$^{++}$, the cation Zn$^{++}$, or a cation of a metal from the lanthanide or actinide group of the Periodic Table; and (iii) carbon monoxide; said reaction being carried out in the presence of a catalyst comprising a salt of cobalt tetracarbonyl hydride, at a temperature ranging from 0° and 200° C., and under a pressure which is less than or equal to 600 bars.

2. The process as defined by claim 1, said organic solvent comprising a carboxylic acid anhydride of the formula (I).

3. The process as defined by claim 1, said organic solvent comprising a polyethylene glycol alkyl ether of the formula:

$$R^5-O-(CH_2-CH_2-O)_y-R^6 \qquad (IV)$$

in which R$^5$ and R$^6$, which may either be identical or different, each has the definition given for R, and y is an integer ranging from 1 to 8.

4. The process as defined by claim 1, said organic solvent comprising a sulfone of the formula:

in which R$^7$ and R$^8$, which may either be identical or different, each has the definition given for R', or R$^7$ and R$^8$ may together form a single divalent alkylene or alkenylene radical containing from 3 to 6 carbon atoms and optionally 1 or 2 ethylenic double bonds, or a substituted such single radical containing from 1 to 3 alkyl substituents having from 1 to 4 carbon atoms.

5. The process as defined by claim 4, wherein R$^7$ and R$^8$ are identical and each is a linear alkyl radical.

6. The process as defined by claim 1, said organic solvent comprising tetramethylenesulfone, 3-methyltetramethylenesulfone, 2,4-dimethyltetramethylenesulfone, or mixtures thereof.

7. The process as defined by claim 1, said organic solvent comprising a carboxylic acid amide of the formula:

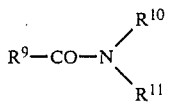

in which $R^9$, $R^{10}$ and $R^{11}$, which may either be identical or different, each has the definition given for R', or any two of the radicals $R^9$, $R^{10}$ or $R^{11}$ may together form a single divalent radical —$(CH_2)_z$—, with z being an integer ranging from 3 to 12; with the proviso that $R^9$ may also be a hydrogen atom or a radical of the formula:

in which $R^{12}$ and $R^{13}$, which may either be identical or different, are alkyl radicals having at most 4 carbon atoms.

8. The process as defined by claim 1, said organic solvent comprising N-methylpyrrolidin-2-one.

9. The process as defined by claim 1, said organic solvent comprising acetonitrile.

10. The process as defined by claim 1, said carboxylate of the formula (III) comprising an alkali metal carboxylate.

11. The process as defined by claim 1, said carboxylate of the formula (III) comprising an acetate.

12. The process as defined by claim 1, the concentration of the carboxylate of the formula (III) in said aprotic organic solvent ranging from 0.1 to 5 mols per liter.

13. The process as defined by claim 12, the molar ratio of the compound of the formula (II) to the carboxylate anion (R'COO$^-$) ranging from 0.5 to 2.

14. The process as defined by claim 1, said catalyst comprising lithium tetracarbonylcobaltate, sodium tetracarbonylcobaltate or methyltriphenylphosphonium tetracarbonylcobaltate.

15. The process as defined by claim 1, said catalyst being formed in situ from dicobalt octacarbonyl.

16. The process as defined by claim 1, the compound of the formula (II) comprising methyl iodide.

17. The process as defined by claim 1, the reaction temperature ranging from 20° to 150° C.

18. The process as defined by claim 17, the pressure at the reaction temperature ranging from 1 to 100 bars.

19. The process as defined by claim 2, said organic solvent comprising a carboxylic acid anhydride of the formula (I) which is identical to the product anhydride.

20. The process as defined by claim 1, said salt of cobalt tetracarbonyl hydride having the formula:

$$M^{p+}[Co(CO)_4]_p$$

in which p is an integer equal to 1 or 2, and $M^{p+}$ is an alkali or alkaline earth metal cation, a cation $N^+R^1R^2R^3R^4$ or $P^+R^1R^2R^3R^4$, or an $Ag^+$, $Mn^{2+}$, $Zn^{2+}$, $Co^{2+}$ or $Hg^{2+}$ cation.

* * * * *